(12) United States Patent
Pautz et al.

(10) Patent No.: US 9,885,643 B2
(45) Date of Patent: Feb. 6, 2018

(54) REAGENT FOR CLARIFYING EMULSIONS AND METHOD OF CLARIFICATION

(71) Applicant: Bentley Instruments S.A.R.L., Lille (FR)

(72) Inventors: Norbert Pautz, Riehen (CH); Pierre Broutin, Lille (FR)

(73) Assignee: Bentley Instruments S.A.R.L., Lille (FR)

( * ) Notice: Subject to any disclaimer, the term of this patent is extended or adjusted under 35 U.S.C. 154(b) by 495 days.

(21) Appl. No.: 14/533,818

(22) Filed: Nov. 5, 2014

(65) Prior Publication Data

US 2015/0056625 A1 Feb. 26, 2015

Related U.S. Application Data

(63) Continuation of application No. PCT/EP2012/001979, filed on May 8, 2012.

(51) Int. Cl.
| | | |
|---|---|---|
| *G01N 31/00* | (2006.01) | |
| *G01N 1/34* | (2006.01) | |
| *B01D 17/04* | (2006.01) | |
| *G01N 1/38* | (2006.01) | |
| *C12Q 1/02* | (2006.01) | |
| *C12Q 1/68* | (2006.01) | |
| *G01N 21/64* | (2006.01) | |
| *G01N 33/50* | (2006.01) | |

(52) U.S. Cl.
CPC .............. *G01N 1/34* (2013.01); *B01D 17/047* (2013.01); *C12Q 1/02* (2013.01); *C12Q 1/6806* (2013.01); *G01N 1/38* (2013.01); *G01N 21/64* (2013.01); *G01N 33/5005* (2013.01)

(58) Field of Classification Search
CPC ......................................... G01N 1/34
USPC .......................................... 436/8
See application file for complete search history.

(56) References Cited

U.S. PATENT DOCUMENTS

| 4,708,939 A | 11/1987 | Siedel et al. |
| 2004/0163671 A1 | 8/2004 | Fournel et al. |

FOREIGN PATENT DOCUMENTS

| EP | 0130537 A2 | 1/1985 |
| EP | 0573054 A1 | 12/1993 |

OTHER PUBLICATIONS

International Search Report re PCT/EP2012/001979, dated Aug. 11, 2012, 2 pgs.

*Primary Examiner* — Jezia Riley
(74) *Attorney, Agent, or Firm* — Greenberg Traurig, LLP

(57) ABSTRACT

A novel reagent for clarification of an emulsion containing a salt and first and second surfactants is used in a method of clarifying emulsions which may contain inorganic, organic or biological particles to be measured. The reagent may be proved as kit of parts for in situ preparation thereof.

28 Claims, 3 Drawing Sheets

| Test No | Invention | BactoCount | Log Invention | BactoCount |
|---|---|---|---|---|
| 1 | 72 | 62 | 1,85 | 1,79 |
| 2 | 173 | 177 | 2,24 | 2,25 |
| 3 | 303 | 335 | 2,48 | 2,53 |
| 4 | 886 | 1000 | 2,95 | 3,00 |
| 5 | 34 | 31 | 1,53 | 1,49 |
| 6 | 82 | 87 | 1,91 | 1,94 |
| 7 | 163 | 129 | 2,21 | 2,11 |
| 8 | 246 | 269 | 2,39 | 2,43 |
| 9 | 429 | 471 | 2,63 | 2,67 |

Reference Method: BactoCount® method (Bentley Instruments)

| Invention (cells/µL) | Ref. Method (cells/µL) |
|---|---|
| 0 | 0 |
| 199 | 199 |
| 394 | 397 |
| 591 | 596 |
| 831 | 795 |
| 1025 | 993 |
| 1217 | 1192 |
| 1393 | 1390 |
| 1582 | 1639 |

Sy,x  29,0002718
Mean  800,111111
CV    3,62453056

Reference Method: BactoCount® method (Bentley Instruments)

| Invention (cells/µL) | Ref. Method (cells/µL) |
|---|---|
| 0 | 0 |
| 208 | 199 |
| 465 | 397 |
| 590 | 596 |
| 819 | 795 |
| 996 | 993 |
| 1247 | 1192 |
| 1415 | 1390 |
| 1642 | 1639 |

Sy,x     27,4543969
Mean    800,111111
CV       3,43132304

ND METHOD OF CLARIFICATION

REAGENT FOR CLARIFYING EMULSIONS AND METHOD OF CLARIFICATION

CROSS REFERENCE TO RELATED APPLICATION

This application is a continuation of International Patent Application Serial No. PCT/EP2012/001979, filed May 8, 2012, which is incorporated herein by reference in its entirety.

FIELD OF THE DISCLOSURE

The present invention relates to a reagent for clarifying oil/fat-in water (O/W) emulsions and a method of clarifying such emulsions in which the reagent is used as well as to a kit of parts comprising the components of the reagent for the in situ preparation thereof.

BACKGROUND OF RELATED ART

The clarification of O/W emulsions to the point where they are a transparent liquid is particularly important for analytical purposes. For example, solid insoluble particles in an emulsion can, if at all, only be determined with difficulties. If the emulsion is not clarified at least to the point where it is translucent, a count of solid insoluble particles in the emulsion by e.g. optical methods is not possible.

The quantification of biological contamination in emulsions is of particular importance, since emulsion in all areas where they are employed, but in particular in food, beverages and healthcare and/or cosmetic products, may become unusable and/or a health risk when the contamination by bacteria, yeast or algae exceeds certain threshold values.

With respect to determination of living microorganisms in emulsions it is highly desirable, to have a reagent and method which can clarify the emulsion into a completely transparent liquid in as short a time and at as low a temperature as possible in order to allow a fast and correct direct quantitative determination of the organisms e.g. by optical means. If the clarification of the emulsion is not complete, the counts may be incorrect e.g. due to remaining particle-like aggregates, and if the temperature is too high and the processing time is too long, the microorganisms may on one hand be destroyed, or, on the other hand, may proliferate both leading to false test results.

In particular with respect to milk which is a fat-in-water emulsion there are a number of methods described in the prior art which aim at the clarification of milk to form a transparent liquid (see e.g. U.S. Pat. No. 3,679,365 A, EP 0246987 B1, DE OS 17089 A1, DE 4017398 A1 and EP 0573054; the entire disclosure of all of these documents is herewith incorporated by reference into this specification). However, none of these methods proved to be satisfying under conditions of routine use.

It was the aim of the present invention to find a more satisfying solution for turning emulsions into transparent liquids.

SUMMARY

In a first aspect, the invention relates to a reagent for clarifying oil/fat-in-water emulsions (also termed O/W emulsions) comprising an aqueous solution of one or more salts having a water solubility of at least about 1 mole/l, one or more first nonionic surfactant(s) having an hydrophilic-lipophilic balance (HLB) value of from about 8.0 to about 13.0 and a Cloud Point of from about 0° C. to about 45° C. and one or more second nonionic surfactant(s) having a an HLB value of about 13.1 to about 16.9 and a Cloud Point of about 59° C. to about 100° C. wherein the reagent has a Cloud Point of equal to or less than about 57° C.

In a further aspect the invention is directed to the use of such reagent for clarifying an O/W emulsion.

In yet another aspect the invention concerns a method of clarifying an O/W emulsion, wherein a reagent according to the invention is added to the emulsion in a predetermined amount and the mixture of the reagent and the emulsion is kept at room temperature or heated to an elevated temperature up to about the boiling point of the mixture and kept for a sufficient period of time at the temperature, until the emulsion has clarified and turned into a transparent liquid.

Still another aspect of the invention concerns a kit of parts for preparing the reagent of the invention in situ, comprising said one or more salts, said one or more first surfactants, said one or more second surfactants and optionally said buffer in at least two separate containers.

DETAILED DESCRIPTION

Figure 1:
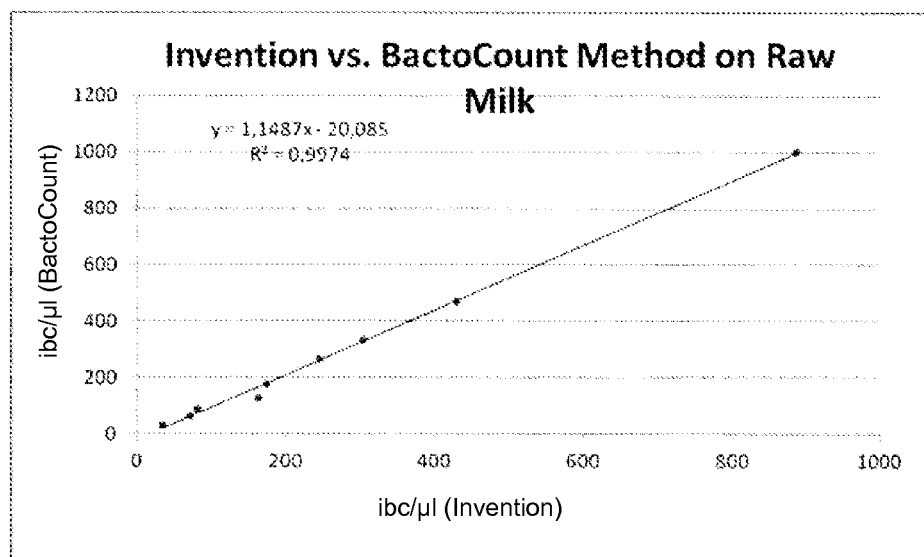
FIG. 1 is a diagram showing the correlation between a determination of bacteria counts in a raw milk sample according to an embodiment of the method of the present invention and according to the BACTOCOUNT® method (Bentley Instruments).

The following description of example methods and apparatus is not intended to limit the scope of the description to the precise form or forms detailed herein. Instead the following description is intended to be illustrative so that others may follow its teachings.

The first aspect of the invention relates to a reagent for clarifying O/W emulsions.

O/W emulsions are well-known to the person skilled in the art and are used in a wide variety of different application areas. Examples are technical emulsions, e.g. cooling lubricants, household emulsions, e.g. dishwashing detergents, emulsion used for cosmetic, healthcare and pharmaceutical products, e.g. facial creams, body lotions and various pharmaceutical creams, and food and beverage emulsions, e.g. ice cream, yogurt, cream, milk and other dairy products.

In many instances, in particular for analytical purposes, a clarification of such emulsions into at least translucent or completely clear transparent water-like liquids by means of a suitable reagent is desirable. The reagent should meet two important requirements: to clarify an O/W at a relatively low temperature and to achieve this in a relatively short time. Moreover, the reagent should be compatible with possible microorganisms in the emulsions, i.e. neither cause the destruction nor cause the proliferation thereof.

It was surprisingly found that a reagent comprising one or more salts and two different kinds of surfactants or mixtures of nonionic surfactants, as described in the above Summary of the Invention, meets these requirements.

The salt contained in the reagent of the present invention must have a high water solubility of at least 1 mole/liter. High salt concentrations are capable to inhibit the lysis of microorganisms which might otherwise be induced by the nonionic surfactants in the reagent.

If microorganisms in an emulsion which is to be treated with the reagent of the invention are to be detected, it is sometimes preferably that the salt(s) therein do not comprise $Na^+$ and $K^+$ ions in higher than physiological concentrations, i.e. 154 mmoles/l and 4 mmoles/l, since they may sometimes contribute to the lysis of microorganisms.

Since the ammonium cation usually provides for very good water solubility and is physiologically compatible, it is the preferred cation in the salt(s) of the reagent.

Also for the reason of good water solubility of the salt(s) of the reagent, the anion(s) thereof are preferably selected from chloride, fluoride, nitrate, formate and acetate.

Ammonium chloride and ammonium formate are particularly preferred salts, whether alone or in admixture.

The total concentration of the salt(s) in the reagent is usually about 0.5 to about 12 moles/l, more often about 1.5 to about 5 moles/l, and particularly preferred about 1.5 to about 2.5 moles/l.

The first nonionic surfactant(s) has or each have an HLB value of from about 8.0 to about 13.0 and a Cloud Point of from about 0° C. to about 45° C., whereas the second nonionic surfactant(s) has or each have an HLB value of from about 13.1 to about 16.9 and a Cloud Point of about 59° C. to about 100° C. (The HLB values herein are the well-known ones for nonionic surfactants according to Griffin).

Nonionic surfactants are well-known to the person skilled in the art (see e.g. Jean-Louis Salager, SURFACTANTS, Types and Uses, FIRP BOOLKET #E300-A (2002), Chapter 4—Nonionic Surfactants, incorporated herewith by reference into this document). Nonionic surfactants are usually selected from Ethoxylated Linear Alcohols (also designated Polyoxyethylene alkyl ethers, Fatty Alcohol Ethoxylates or CnEm), Ethoxylated Alkyl Phenols, Fatty Acid Esters, Amine and Amide Derivatives, Alkylpolyglucosides, Ethyleneoxide/Propyleneoxide Copolymers, Polyalcolols and ethoxylated polyalcohols, Thiols (mercaptans) and derivates.

It is well-known to the person skilled in the art that the capability of a nonionic surfactant to dissolve oil or fat increases with an increase of the HLB value. Therefore a surfactant having a high HLB value is necessary for clarifying O/W emulsion having a high oil or fat content. On the other hand, a high HLB value is usually accompanied by a high Cloud Point temperature (although that temperature also depends on other parameters, see below). This means that a mixture comprising an emulsion and a surfactant having a high Cloud Point temperature must be heated to approximately the latter temperature in order to initiate clarification of the mixture which is undesirable when microorganisms have to be determined, since they undergo lysis even in nonionic surfactants at higher temperatures. Upon cooling below the Cloud Point the nonionic surfactants agents form micelles. These micelles are much smaller than the wavelength of light so the solution becomes transparent and the solubility of the oil/fat increases significantly.

The reagent of the invention is required to have a Cloud Point of a maximum of 57° C. which is the upper limit of compatibility with living microorganisms. More preferably, the Cloud Point does not exceed 53° C. Single surfactants having a high HLB value of 13.1 or more do not have such a low Cloud Point. Therefore, a second surfactant having a lower Cloud Point is used in combination with the first surfactant. This lowers the Cloud Point, but also the HLB, i.e. the oil/fat dissolving properties of the mixture.

The resulting HLB value of a mixture of two surfactants can easily be calculated ((mass % of surfactant 1 in the mixture)×HLB thereof+(mass % of surfactant 2 in the mixture)×HLB thereof=HLB of mixture). However, such an easy calculation of the Cloud Point of a mixture is not possible.

As mentioned above, the Cloud Point (CP) depends on the HLB, but is also a function concentration of the surfactants and the salts. Beyond a certain critical concentration the CP decreases monotonically with increasing salt concentration. Furthermore, it is also known that the effect of adding salts will reduce the effective HLB value of the clarification reagent so the proper balance needs to be found.

Therefore, there is always a certain amount of experimentation required to find the best compromise between a desired HLB and a given Cloud Point (or between a desired Cloud Point and a given HLB) for the choice of surfactants and salt(s) used in the mixture.

As a general rule, however, a relatively low HLB value of about 13.0 to about 14 is sufficient when the proportion of oil/fat in the emulsion is low, e.g. around 1% by weight. In this case, the first surfactant(s) may comprise the major amount of the surfactant mixture, and the second surfactant(s) comprise only a minor amount of the surfactant mixture. For emulsions with a higher fat content, such as raw milk with a fat content of about 3.5 to about 4% by weight or cream with a fat content of up to 50%, a higher HLB, e.g. of about 14.5 to about 15 is required to achieve clarification into a clear solution. In this case, the amount of second surfactant(s) in the mixture will be significantly greater than the amount of the first surfactant(s).

Examples of the first surfactant having an HLB value of from about 8.0 to about 13.0 and a Cloud Point of from about 0° C. to about 45° C. are: TRITON® X-114 (The Dow Chemical Company), a proprietary mixture of polyoxyethylene monooctylphenyl ether with 7-8 oxyethylene units (Cloud Point (CP): 23° C., HLB value: 12.4), which is particularly preferred, Unitol Hydol-6 (C8E3; CP: 38-42° C., HLB value: 11.5) and the following proprietary surfactants: LUTENSOL® TDA 6 (HLB value: 11.0, CP: 41° C.), TRITON® X45 (HLB value: 9.6 CP: 38° C.), PLURAFAC® LF-400 (HLB value: 9.0, CP: 35° C.), PLURAFAC® SL-42 (HLB value: 13.0, CP: 42° C.), IGEPAL® CA 620 (HLB value: 12.0, CP: 22° C.), and IGEPAL® CO-610 (HLB value: 12.6, CP: 26° C.).

Examples of the second surfactant having an HLB value of from about 13.1 to about 16.9 and a Cloud Point of about 59° C. to about 100° C. are: Walloxen ID 110 (Wall Chemie GmbH, Kempen, Germany), a polyoxyethylene isodecyl ether ("isodecylalcohol-11-polyglycol ether") (HLB value 15.1, CP: 62-66° C.,), which is particularly preferred, LANSPEC® EMP906C, a proprietary C13 alcohol ethoxylate (HLB value: 13.5, CP: 68-72° C.) and TERGITOL® 15-S-9 (The Dow Chemical Company), a proprietary secondary alcohol ethoxylate (HLB value 13.3, CP: 60° C.) and the following proprietary surfactants: TRITON® X 100 (HLB value: 13.5 CP: 65° C.) BRIJ® 35 (HLB value: 16.9, CP>100° C.), TWEEN® 20 (HLB value: 16.7, CP: 95° C.), TWEEN® 80 (HLB value: 15.0, CP: 60° C.), and NONIDET® P40 (HLB value: 13.5, CP: 63-67° C.).

As already indicated above, the weight ratio of the first surfactant(s) to the second surfactant(s) may vary widely, e.g. from about 1:6 to about 6:1, more preferred from about 1:3 to about 3:1 and particularly preferred from about 1:2 to about 2:1. The weight ration mainly depends on the amount of fat in the emulsion, but also on the amount of salt(s) in the reagent and in the emulsion, which influences the stability and dissolution, respectively, of emulsions, and on other non-fat or non-oil components which may interfere with the clarification.

The ratio between the salts and the combined weight of the surfactants may also vary widely, e.g. from about 0.5 mole of salt(s) per 100 g of total surfactants to about 2 moles of salt(s) per 100 g of total surfactants.

The total concentration of the first surfactant(s) and the second surfactant(s) in the reagent may vary e.g. from about 100 g/l to about 500 g/l, more often from about 160 g/l to about 380 g/l, and in particular about 175 g/l to about 275 g/l. The total concentration of the first surfactant(s) may be e.g. from about 15 g/l or about 25 g/l or about 50 g/l or about 75 g/l to about 120 g/l or about 180 g/l or about 300 g/l or about 430 g/l. The total concentration of the second surfactant(s) may be within the same ranges.

The reagent of the invention may optionally contain a buffering agent in addition to the salts, or, if the buffering agent only comprises salts, as the salts of the reagent of the invention. A suitable buffer agent only comprising salts is e.g. Bentley Instruments, IBCM BactoKit 500 Component 1, comprising sodium borate decahydrate, sodium carbonate and EDTA dihydrate, which may be contained in the reagent in a proportion of about 1% to about 5% by weight.

Furthermore, the reagent may comprise one or more fluorescent dyes.

The reagent of the invention may also contain minor amount of non-essential components, such as minor amounts of organic solvents, e.g. alcohols, ethers, esters, ketones and aldehydes, or colorants.

Thus, the reagent may consist or may consist essentially of the above mentioned salt(s) and first and second nonionic surfactants and optionally a buffer and one or more fluorescent dyes.

A particularly preferred reagent according to the invention comprises about 130 to about 150 g/l of isodecylalcohol-11-polyglycolether (Walloxen ID 110/80), about 65 to about 75 g/l of TRITON® X-114, about 110 to about 130 g/l of ammonium formate and optionally a fluorescent dye and has a Cloud Point of from about 51 to about 53° C.

The preparation of the reagent of the invention is simple, but the following order has to be observed: at first, the salt and possibly the buffer salt is added to deionized or distilled water, if necessary with gentle heating. At that temperature or after cooling to ambient temperature the second surfactant (s) is/are added, and thereafter the first surfactant(s) is/are added. If the mixture is still warm when the surfactants are added, it may become turbid, but upon cooling to ambient temperature the mixture will turn into a clear solution ready for use.

The above-described reagent is used for clarifying O/W emulsions into translucent or transparent solutions.

In the method of the invention, the above-described reagent is added to an emulsion in a predetermined amount whereupon the mixture obtained is either kept at room temperature or at an elevated temperature up to the boiling point of the mixture until the emulsion has turned into a translucent or transparent liquid.

As mentioned above, the method of the invention can be performed with any emulsion, such as technical emulsions, e.g. cooling lubricants, household emulsions, e.g. dishwashing detergents, emulsion used for cosmetic, healthcare and pharmaceutical products, e.g. facial creams, body lotions and various pharmaceutical creams, and food and beverage emulsions, e.g. and other dairy products.

The emulsion may be diluted before the clarifying reagent is added, for example if the oil/fat concentration or concentration of other components in the emulsion is too high and might interfere with the clarification and/or the measurement of the desired parameter, e.g. number of particles/microorganisms in the emulsion.

The amount of reagent necessary to clarify the emulsion to a translucent or transparent liquid may vary widely and depends on a variety of parameters, such as kind of oil or fat, concentration of oil or fat, concentration of electrolytes, concentration of other neutral substances etc. It is usually predetermined by preliminary serial experiments wherein at first a coarse range of the necessary amount is established and then the amounts are tested in smaller intervals. The person skilled in the art is familiar with such routine testing. The concentration employed should be as low as possible, if testing of microorganisms is involved so as to insure their viability or at least their integrity.

There are circumstances where the emulsion can be clarified by the reagent of the invention at room temperature (about 25° C.), which is highly desirable when microorganisms are to be tested, since in this case their viability or at least integrity is insured. However, often the mixture of emulsion and clarifying reagent has to be heated for clarification. This may be up to the boiling point of the emulsion, if the latter does not contain any heat-sensitive components. The required temperature is highly dependent on the specific nature of the emulsion, as in the case discussed above for the amount of reagent, and usually preliminary routine experiments are required to find the best temperature and period of reaction time for a specific emulsion. At any rate, the reaction is complete, when the mixture has completely clarified and turned into a translucent or transparent solution.

The emulsion to be clarified may or may not contain inorganic, organic or biological particles which are insoluble in the aqueous medium after clarification.

A property which may be measured on a clarified emulsion not containing any particles is e.g. the color of any dissolved colored compounds by means of UV/Vis spectroscopy.

If particles are present, their characteristics, e.g. their concentration, may much more easily or may only be measured after clarification of the emulsion by any analytical method used by the person skilled for measurements of particles present in a medium which is a solvent or an ordinary clear solution.

Emulsions which contain biological particles, i.e. microorganisms (bacteria, yeasts, algae) and possibly somatic cells, are of particular importance in connection with the present invention. Microorganisms and possibly somatic cells may be present in all kinds of emulsions in extremely varying concentrations, such as from virtually zero (in freshly sterilized products) or 1000 to say 20 million biological particles (e.g. in raw milk) per ml. Since microorganisms may spoil all types of emulsion, and most importantly food and beverage emulsions, their quantitative and qualitative determination is of highest interest.

It was surprisingly discovered that the present method is useful in emulsions containing microorganisms to be measured even if heating of the mixture of emulsion and reagent to about 56.5° C., or more preferred to about 45° C. up to about 55° C., for a time of up to about 20 minutes, such as 12 minutes, preferably up to about 10 minutes, and most preferably up to about 2 minutes, is required for complete clarification of the emulsion, as is e.g. the case with raw milk.

It is to be expected that a small part of microorganisms may undergo lysis under these conditions. If, however, after measuring the number of microorganisms in the emulsion clarified according to the method of the invention, there is a linear correlation over the interesting range of concentrations with a method which is known to yield correct counts, the method is valid and can be used for a correct determination of the amount of cells. Surprisingly, such a linear correlation was indeed found for the method of the present invention when the amount of microorganisms in a raw milk sample was tested.

FIG. 1 shows the correlation between microorganism counts (unit: ibc (individual bacteria count)/µl) performed on a raw milk sample by means of the method performed by an automatic BACTOCOUNT® instrument (Bentley Instruments) (a method already internationally recognized for the rapid determination of total bacteria in raw milk) and the method according to the invention wherein the raw milk sample was clarified as described in Example 2 and the microorganisms where then counted by means of flow cytometry. The correlation is excellent which means that any loss of microorganism (mostly bacterial) particles, i.e. cells, due to lysis is proportional to the number of microorganisms in the sample and can be taken account of by calibrating the method.

Figure 2:
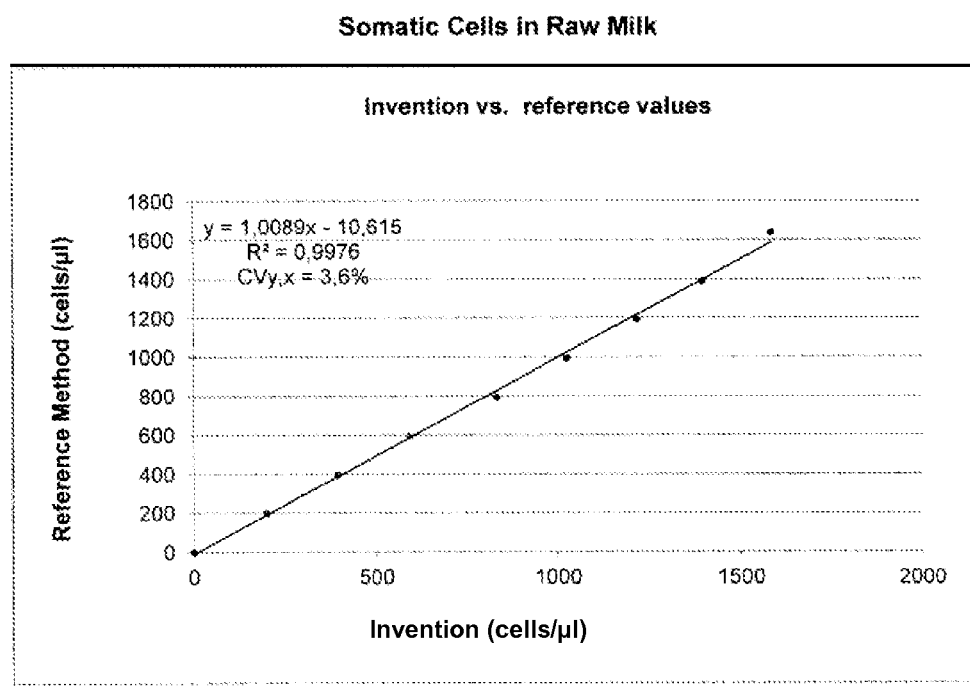
FIG. 2 is a diagram showing the correlation between a determination of somatic cells counts in a raw milk sample according to another embodiment of the method of the present invention and according to the BACTOCOUNT® method (Bentley Instruments).

FIG. 2 is a diagram showing the correlation between a determination of somatic cells counts in a raw milk sample according to the method of the present invention as described in Example 5 and according to the BACTOCOUNT® method (Bentley Instruments). The correlation is excellent.

Figure 3:
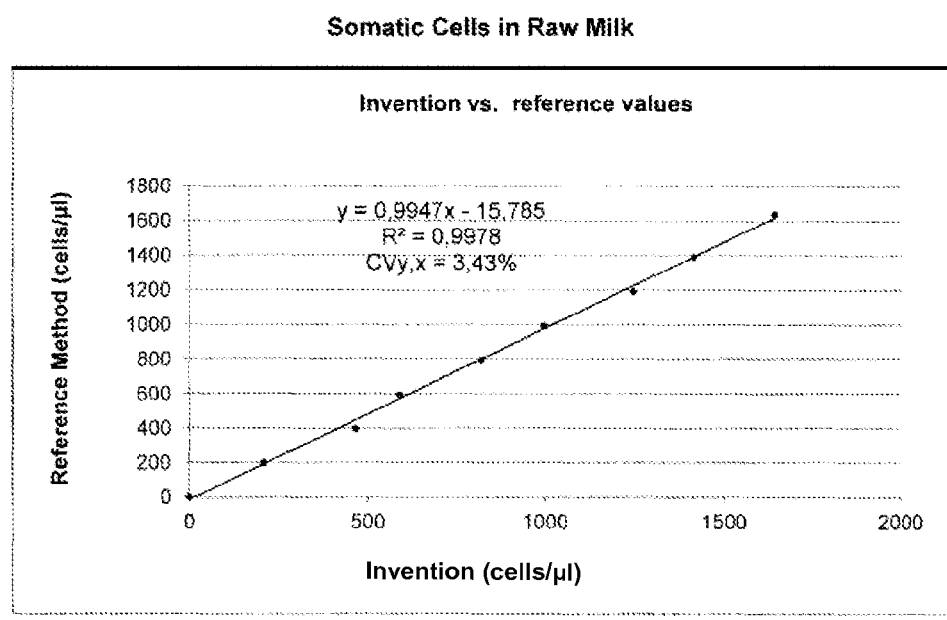
FIG. 3 is a diagram showing the correlation between a determination of somatic cells counts in a raw milk sample according to still another embodiment the method of the present invention and according to the BACTOCOUNT® method (Bentley Instruments).

FIG. 3 is a diagram showing the correlation between a determination of somatic cells counts in a raw milk sample according to the method of the present invention as described in Example 6 and according to the BACTOCOUNT® method (Bentley Instruments). The correlation is excellent.

For milk or other dairy products, the reagent of the invention preferably has a Cloud Point of equal to or less than 55° C., preferably of about 51 to about 53° C., and preferably the first nonionic surfactant thereof is TRITON® X-114, the second nonionic surfactant is isodecylalcohol-11-polyglycolether (Walloxen ID 110) and the salt is ammonium formate.

A buffer salt may be included in the reagent, as described above.

As mentioned above, the amount of reagent added to an emulsion sample for completely clarification usually has to be established by routine serial experiments. It was found by such experiments that the amount of reagent added to 1 ml of raw milk advantageously contains a total amount of the first surfactant(s), preferably TRITON® X-114, of from about 100 mg to about 320 mg, particularly preferred from about 190 mg to about 230 mg, a total amount of the second surfactant(s), preferably isodecylalcohol-11-polyglycolether, of from about 280 mg to about 530 mg, particularly preferred from about 400 mg to about 450 mg, and a total molar amount of from about 1 mmole to about 15 mmoles, particularly preferred from about 5.5 to about 6.5 mmoles, of said one or more salts, preferably ammonium formate, buffer salts not included. This amount may be contained in 3 ml of reagent.

Furthermore, the pH of the mixture of emulsion sample and reagent should usually be controlled to be in a pH range of about neutral to about 9.5. The pH value may be adjusted before, while or after the reagent is added. The pH adjustment may be accomplished by selection of appropriate salt(s) (e.g. acidic or basic) and the concentration thereof in the reagent, by adding a suitable buffer to the emulsion and/or by adding a suitable buffer to the reagent. Suitable buffers for the above pH ranges are well-known to the person skilled in the art.

When detecting microorganisms in an emulsion, in particular in milk and dairy products, one or more proteolytic enzymes may be added before, while or after the reagent is added so as to destroy larger protein aggregates which might interfere with the measurement. Proteolytic enzymes and their methods of use are well-known to the person skilled in the art.

Furthermore one or more fluorescent dyes may be added to the emulsion before, while or after the reagent is added, if the microorganisms are detected by an optical method requiring fluorescence staining. Suitable fluorescence dyes and their use are well-known to the person skilled in the art.

As mentioned above, the nature and/or the amount of insoluble organic, organic or biological particles in the clarified emulsion may be determined by any suitable method, including chemical methods. Preferred methods for the qualitative and quantitative detection of particles are optical, physical and biochemical methods. They include analysis by means of ICP (Inductively-Coupled Plasma), Flow Injection Analyzers, Flow Cytometers, spectrometry (visible, infrared, UV, fluorescence), CCD cameras, light microscopy and fluorescence microscopy and PCR (polymerase chain reaction). These methods are well-known to the person skilled in the art.

A kit for producing the reagent of the invention in situ comprises the one or more salts, the one or more first surfactants, the one or more second surfactants and optionally buffer salt in at least two separate containers. Preferably, each reagent is contained in a separate container. The kit may also include instructions for the preparation of the reagent and for its use in a specific method of clarifying an emulsion, e.g milk or another dairy product.

The following examples illustrate the invention without the intention to limit the scope thereof.

EXAMPLES

Example 1—Preparation of a Reagent for Clarifying a Raw Milk Emulsion 10 g of ammonium formate for analysis (Aldrich) were dissolved in 60 ml in-house deionized sterile water with stirring at room temperature. 12 g of WALLOXEN® ID 110 (80% in water) were added and thereafter 6 g of TRITON® X-114. The solution was clear at room temperature.

The Cloud Point was determined experimentally. The reagent was heated up until it became turbid. It was then the cooled down until the reagent become transparent again. The temperature at which the reagent changed from transparent to cloudy phase was recorded and defined as the Cloud Point (CP).

The CP was found to be 52-53° C.

The HLB value was calculated to be approximately 15.

Example 2—Clarification of a Raw Milk Sample and Bacterial Count

A 1 ml sample of raw milk and 3 ml of the reagent prepared in Example 1 were mixed, and 2.0 ml of Bentley IBCM BactoKit 500 reagent (buffer+enzyme+fluorescent dye) were subsequently added to 1 ml of the clarified mix. The resulting mixture was incubated at 50±5° C. for 10 minutes and sonicated for 16 sec.

The number of cells (mostly bacteria) was determined by flow cytometry and compared to the result determined on another sample of the same milk by means of an automatic BACTOCOUNT® instrument (Bentley Instruments). The result is shown in FIG. 1.

Example 3—Clarification of a Raw Milk Sample and Bacterial Count and Identification by Polymerase Chain Reaction (PCR)

A 1 ml sample of raw milk was clarified as described in Example 2, however, no proteolytic reagent was added.

Then the total DNA of the clarified milk was extracted and subjected to PCR bacterial count and identification by means of a standard protocol (Thermo Scientific PATHOPROOF® Mastitis Complete-12 PCR assay).

The complete clarification of the milk in this method is of great advantage, because with this method no milk clots and fat have to be removed after centrifugation. Filtration of the samples is also much easier.

Example 4—Preparation of a Reagent for Clarifying a Raw Milk Emulsion 10 g of ammonium formate for analysis (Aldrich) were dissolved in 60 ml in-house deionized sterile water with stirring at room temperature. 12 g of WALLOXEN® ID 110 (80% in water) were added, thereafter 6 g of TRITON® X-114 and finally 10 μg of Phenantridinium fluorescent dye. The solution was clear at room temperature. The pH value was approximately 7.0.

Example 5—Clarification of a Raw Milk Sample and Rapid Quantification of Somatic Cells 1 ml of raw milk was mixed with 1 ml of the reagent of Example 4 and 1 ml of a dye solution (Bentley IBCM BactoKit Component 3), and after 10 sec incubation at room temperature somatic cells count was determined by flow cytometry and compared to the result determined on another sample of the same milk by means of the BACTOCOUNT® method (Bentley Instruments). The result is shown in FIG. 2.

Example 6—Clarification of a Raw Milk Sample and Rapid Quantification of Somatic Cells 1 ml of raw milk was mixed with 3 ml of the reagent of Example 4 and incubated at 54° C. for 3 minutes until complete clarification (transparency).

1 ml of the above clarified mix and 2 ml of 50% dye solution (Bentley IBCM BactoKit Component 3) in water were incubated for 10 sec at room temperature. Then the somatic cells count was determined by flow cytometry and compared to the result determined on another sample of the same milk by means of the BACTOCOUNT® method (Bentley Instruments). The result is shown in FIG. 3.

Example 7—Preparation of a Reagent for Clarifying Cooling Lubricant 9.8 g of ammonium chloride were added to 45 ml of distilled water with gentle heating to 40° C. Then 2.3 g of LANSPEC® EMP906 and thereafter 5 g of TRITON® X-114 were added. After cooling to room temperature a clear solution was obtained.

Example 8—Clarification of a Cooling Lubricant Emulsion Containing Microorganisms The reagent of Example 7 was added to a sample of cooling lubricant emulsion contaminated with microorganisms in a 1:1 ratio by volume. The emulsion turned into a clear yellow liquid immediately after addition of the reagent.

Microorganisms were counted by means of a flow cytometer.

Although certain example methods and apparatus have been described herein, the scope of coverage of this patent is not limited thereto. On the contrary, this patent covers all methods, apparatus, and articles of manufacture fairly falling within the scope of the appended claims either literally or under the doctrine of equivalents.

We claim:

1. A reagent for clarifying oil/fat-in-water (O/W) emulsions comprising:
    an aqueous solution of one or more salts having a water solubility of at least 1 mole/l, one or more first nonionic surfactants having an hydrophilic-lipophilic balance (HLB) value of from about 8.0 to about 13.0 and a Cloud Point of from about 0° C. to about 45° C., and one or more second nonionic surfactants having an hydrophilic-lipophilic balance (HLB) value of about 13.1 to about 16.9 and a Cloud Point of about 59° C. to about 100° C.,
    wherein the reagent has a Cloud Point of equal to or less than about 57° C.,
    wherein the ration of the amount of salt(s) to surfactant(s) is about 0.25 moles to about 2 moles per 100 g of total of surfactant(s) and the concentration of the salt(s) in the reagent is about 0.5 to about 12 moles/l.

2. A reagent as recited in claim 1, wherein the one or more salts do neither comprise $Na^+$ in an amount of greater than 154 mmole/l nor $K^+$ in an amount of greater than 4 mmole/l.

3. A reagent as recited in claim 1, wherein the cation of the one or more salts is $NH_4^+$.

4. A reagent as recited in claim 1, wherein the anion(s) of the one or more salts are selected from the group consisting of chloride, fluoride, nitrate, formate, and acetate.

5. A reagent as recited in claim 1, wherein the one or more salts are selected from the group consisting of ammonium chloride and ammonium formate.

6. A reagent as recited in claim 1, wherein the salt comprises a buffering mixture of sodium borate decahydrate, sodium carbonate, and EDTA dihydrate.

7. A reagent as recited in claim 1, wherein the ratio of the one or more first nonionic surfactants to the one or more second nonionic surfactants is from about 6:1 to about 1:6 by weight.

8. A reagent as recited in claim 1, wherein the one or more first surfactants is selected from TRITON® X-114.

9. A reagent as recited in claim 1, wherein the one or more second surfactants is selected from isodecyl-11-polgylcolether (Walloxen ID 110).

10. A reagent as recited in claim 1, wherein the total concentration of the first surfactant(s) and the second surfactant(s) in the aqueous solution is from about 100 g/l to about 500 g/l.

11. A method of clarifying an O1W emulsion comprising:
    adding a reagent according to claim 1 to an emulsion in a predetermined amount;

maintaining the mixture of the reagent and the emulsion between room temperature and an elevated temperature up to about the boiling point of the mixture for a sufficient period of time, until the emulsion has clarified and turned into a translucent or transparent liquid.

12. A method as recited in claim 11, wherein the emulsion contains inorganic, organic, or biological particles which are insoluble in the transparent liquid.

13. A method as recited in claim 12, wherein the reagent according to claim 2 is added, the particles are biological particles, and a temperature of 56.5° C. is not exceeded.

14. A method as recited in claim 11, wherein the emulsion is selected from the group consisting of technical emulsions, household emulsions, emulsions used in cosmetic products, emulsions used in healthcare products, emulsions used in pharmaceutical products, food emulsions, and beverage emulsions.

15. A method as recited in claim 14, wherein the emulsion is selected from milk and dairy products.

16. A method as recited in claim 15, wherein the method involves a maximum temperature in the range of from more than about 37° C. to about 56.5° C. over a maximum period of time of about 20 minutes.

17. A method as recited in claim 16, wherein the method involves an incubation at a temperature of about 45 to 55° C. over a maximum period of time of about 10 minutes.

18. A method as recited in claim 15, wherein the hydrophilic-lipophilic balance (HLB) value of the reagent is 10 or higher to obtain a translucent to transparent solution, and 13 or higher to obtain a transparent solution.

19. A method as recited in claim 13, wherein the reagent has a Cloud Point of equal to or less than 55° C., preferably of about 51 to about 53° C., the first nonionic surfactant is TRITON® X-114, the second nonionic surfactant is iso-decylalcohol-11-polyglycolether, and the salt is ammonium formate.

20. A method as recited in claim 13, wherein the reagent added to 1 ml of milk contains a total amount of the first surfactant(s) of from about 100 mg to about 320 mg, particularly preferred from about 190 mg to about 230 mg, a total amount of the second surfactant(s) of from about 280 mg to about 530 mg, particularly preferred from about 400 mg to about 450 mg, and a total molar amount of from about 1 mmole to about 15 mmoles, particularly preferred from about 5.5 to about 6.5 mmoles, of said one or more salts, buffer salts not included.

21. A method as recited in claim 15, wherein the pH of the milk or dairy product is adjusted to a pH of about 7.0 to 9.5 before, while or after the reagent is added.

22. A method as recite in claim 13, wherein also one or more proteolytic enzymes are added before, while or after or within the reagent is added.

23. A method as recited in claim 13, wherein also one or more fluorescent dyes are added before, while or after or within the reagent is added.

24. A method as recited in claim 13, wherein a sonication treatment is applied to the emulsion or to the mixture of the emulsion and the reagent.

25. A method as recited in claim 12, wherein the nature and/or the amount of insoluble organic, organic or biological particles is determined by optical or physical methods.

26. A method as recited in claim 13, wherein after clarification of the emulsion the DNA contained therein is extracted and subjected to Polymerase Chain Reaction (PCR).

27. A reagent as recited in claim 1, wherein the ratio of the one or more first nonionic surfactants to the one or more nonionic surfactants is from about 1:3 to about 3:1 by weight.

28. A reagent as recited in claim 1, wherein the ratio of the one or more first nonionic surfactants to the one or more nonionic surfactants is from about 1:2 to about 2:1 by weight.

* * * * *